United States Patent
Yoxall et al.

(10) Patent No.: US 10,295,560 B2
(45) Date of Patent: May 21, 2019

(54) NEAR FIELD OPTICAL MICROSCOPE FOR ACQUIRING SPECTRA

(71) Applicant: ASOCIACION CENTRO DE INVESTIGACIÓN COOPERATIVA EN NANOSCIENCIAS (CIC NANOGUNE), Donostia (ES)

(72) Inventors: Edward Yoxall, Tounton Somerset (GB); Martin Schnell, Berlin (DE); Rainer Hillenbrand, San Sebastian (DE)

(73) Assignee: ASOCIACION CENTRO DE INVESTIGACIÓN COOPERATIVA EN NANOSCIENCIAS (CIC NANOGUNE), Donostia (ES)

( * ) Notice: Subject to any disclaimer, the term of this patent is extended or adjusted under 35 U.S.C. 154(b) by 0 days.

(21) Appl. No.: 15/558,156

(22) PCT Filed: Mar. 10, 2016

(86) PCT No.: PCT/EP2016/055173
§ 371 (c)(1),
(2) Date: Sep. 13, 2017

(87) PCT Pub. No.: WO2016/146481
PCT Pub. Date: Sep. 22, 2016

(65) Prior Publication Data
US 2018/0038891 A1   Feb. 8, 2018

(30) Foreign Application Priority Data

Mar. 13, 2015 (EP) .................... 15158965

(51) Int. Cl.
*G01N 21/35* (2014.01)
*G01N 21/39* (2006.01)
*G01Q 60/22* (2010.01)

(52) U.S. Cl.
CPC ............. *G01Q 60/22* (2013.01); *G01N 21/35* (2013.01); *G01N 21/39* (2013.01); *G01N 2021/3595* (2013.01); *G01N 2021/399* (2013.01)

(58) Field of Classification Search
CPC ........ G01Q 60/22; G01N 21/35; G01N 21/39; G01N 2021/3595; G01N 2021/399
USPC ............................................. 850/21, 30, 32
See application file for complete search history.

(56) References Cited

U.S. PATENT DOCUMENTS 8,646,110 B1   2/2014   Xu et al.
8,793,811 B1   7/2014   Prater et al.

FOREIGN PATENT DOCUMENTS

WO   PCT/EP2016/055173   5/2016

OTHER PUBLICATIONS

Huth F. et al., "Infrared-spectroscopic nanoimaging with a thermal source," *Nature Materials*, vol. 10, No. 5, Apr. 17, 2011, pp. 352-356 (Exhibit 3).

(Continued)

*Primary Examiner* — Nicole M Ippolito
*Assistant Examiner* — Hanway Chang
(74) *Attorney, Agent, or Firm* — Adriano & Associates

(57) ABSTRACT

The invention relates to a device for conducting near-field optical measurements of a sample comprising a wavelength-tunable monochromatic light source. Further the invention relates to methods for measuring the near-field using such a device.

15 Claims, 7 Drawing Sheets

(56) References Cited

OTHER PUBLICATIONS

Bek Alpan et al., "Apertureless scanning near field optical microscope with sub-10nm resolution," *Review of Scientific Instruments*, AIP, Melville, NY, US, vol. 77, No. 4, Apr. 4, 2006, pp. 043703-1-043703-11 (Exhibit 4).

Schnell Martin et al., "Amplitude- and Phase-Resolved Near-Field Mapping of Infrared Antenna Modes by Transmission-Mode Shattering-Type Near-Field Microscopy," *Journal of Physical Chemistry C*, 2010, vol. 114, No. 6, Apr. 29, 2010, pp. 7341-7345 (Exhibit 5).

NEAR FIELD OPTICAL MICROSCOPE FOR ACQUIRING SPECTRA

This application is a 371 application of PCT application No. PCT/EP2016/055173, filed Mar. 10, 2016, which claims the priority of EP application No. 15158965.2, filed Mar. 13, 2015, the contents of all of which are hereby incorporated by reference in their entirety into the present application.

The invention relates to a device for conducting near-field optical measurements of a sample comprising a wavelength-tunable monochromatic light source. Further the invention relates to methods for measuring the near-field using such a device.

Scattering-type scanning near-field optical microscopy (s-SNOM) has emerged as a powerful tool for optical and infrared imaging at significantly sub-diffraction-limited length scales, and has been applied to diverse range of research topics including polymer studies, plasmonics, phononics, nanoscale free-carrier densities, biological materials and graphene. It is particularly effective when operated with mid-infrared (IR) radiation, as in this "chemical fingerprint" spectral region the vibrational modes of molecules can be probed to provide non-destructive analysis of a sample's chemical composition. The spatial resolution of traditional infrared-spectroscopic techniques is constrained to around half of the light's wavelength (typically ~5 μm) by the diffraction limit. S-SNOM, on the other hand, circumvents this limit by making use of the enhanced and strongly confined near field that exists at the apex of illuminated sharp probes. As a result, infrared near-field images and spectra can be obtained with a spatial resolution that is determined by the size of the probe's apex (typically ~25 nm).

Optical near-field microscopy is based upon the measurement of light scattered from a near-field probe. The probes used in s-SNOM can be considered as optical antennas that first concentrate the incident field at their tips (where it is affected by a near-field interaction with the sample), and subsequently scatter the light back into the far field. A detector measures the backscattered light, known as the near field. Images are built up by scanning (scan-probing) the sample. Changes in the magnitude or phase of the backscattered light at different positions on the sample create image contrast, which allows various material properties to be determined.

To date, the majority of spectroscopic measurements made with s-SNOM have been performed by either extracting the pixel values of a sequence of consecutively recorded single wavelength images or by using a broadband light source, such as a femtosecond-pulsed lasers, synchrotrons or globars, to perform Fourier transform spectroscopy at individual pixels (nano-FTIR). The former can be time consuming in both data acquisition and post-processing whereas the latter's light sources tend to suffer from low spectral irradiance leading to long measurement times and low spectral resolution.

An alternative approach is to use the spectral tunability and high powers offered by contemporary external cavity quantum cascade lasers (QCLs). These lasers offer the advantage of being able to perform single wavelength imaging, while also being able to "sweep" through their tuning range to gather a full spectrum at any particular point of interest. Previous publications on near-field spectroscopy with a swept QCL source have shown that it is possible to rapidly distinguish substances on a sample surface using such a wavelength-sweep ("Infrared near-field spectroscopy of trace explosives using an external cavity quantum cascade laser," Opt. Express 21, 30401 (2013)), but until now no demonstration has been made in which both the magnitude and phase of the near-field signal have been measured via a swept laser source. Both values are required for a number of important applications; the reconstruction of the sample's local dielectric constant, near-field tomography and, critically for nanoscale chemical identification, the ability to directly compare spectra gathered in the near field with traditionally acquired far-field absorption spectra.

This link between the near-field and far-field spectra is desired due to the fact that the imaginary part of the near-field signal (as measured by s-SNOM) matches well with far-field absorbance spectra in the case of weak molecular oscillators, for example most polymers and biological materials. Given the prevalence of standard infrared spectroscopy tools (such as Fourier transform infrared spectroscopy, or FTIR), large databases of infrared absorption spectra exist. With magnitude and phase-resolved near-field spectroscopy, these same databases could be used in the future for material identification by simply searching for the particular absorbance spectrum that best fits the imaginary part of the near-field spectrum. Using the imaginary part in this way, however, requires that both the magnitude and phase of the near-field signal are recorded.

The general problem of scattering type near-field optical microscopes is that the largest part of the collected light does not originate from the tip apex. Instead, it is mostly produced by reflections and scatterings from the tip shaft and the entire illuminated area of the sample. This undesirable part of the signal is commonly referred to in the art as background signal, or background light. Several methods to avoid the background signal are known in the art.

EP 1 770 714 A1 discloses a method for reducing the background signal by demodulating the scattered light at the frequency of the higher harmonics of the tip oscillation. This way, the near-field signal to background signal ratio can be significantly improved. While the unmodulated background signal is significantly larger than the unmodulated near-field signal, the near-field signal at the first demodulation order and the background signal at the first demodulation order are approximately of the same order of magnitude. At the second demodulation order the near-field signal) becomes significantly larger than the background signal.

A further method for reducing background interference is disclosed in DE 10 035 134. The disclosed method is based on the detection of the scattering at higher harmonics of the tip oscillation frequency, heterodyned with the reference wave shifted by a specific frequency in respect to the light used for tip and sample illumination.

For spectroscopic measurements with monochromatic light sources, the known S-SNOM schemes, such as the pseudo-heterodyne scheme, can be employed in one of two ways. The first way is based on imaging. A single laser wavelength is selected and the sample is raster scanned beneath the probe by a high precision piezoelectric stage. As such, an image is built up pixel by pixel (position by position), and if a number of images are taken at different wavelengths, the spectral characteristics of a particular feature can be extracted from its pixel (position) values. The second way is, as used according to the present invention, where the probe is positioned at a single position on the sample and the laser's wavelength is swept through a spectral range of interest. If the rate of change of wavelength is constant, the elapsed time from the start of the sweep can be directly equated to the lasing wavelength. In this way, the complex near-field spectrum at a single pixel (position) can be measured, in the following termed $\sigma_n(\lambda)$—which is comprised of both a magnitude spectrum, $s_n(\lambda)$, and a phase spectrum, $\phi_n(\lambda)$—within a few seconds. The index n in $s_n(\lambda)$, $\sigma_n(\lambda)$ and $\phi_n(\lambda)$ refers to the demodulation order in the demodulation (of the scattered light at the frequency of the higher harmonics of the tip oscillation) of the detector signal, and typically is n=3.

Both the single wavelength imaging approach and the wavelength sweeping approach also require a reference spectrum, $\sigma_{n,ref}(\lambda)$, to be acquired. The reference spectrum accounts for variations in laser power at different wavelengths, as well as changes caused by other wavelength-sensitive components of the experimental setup. In the imaging approach, this is usually achieved by placing the sample on a substrate with a spectrally flat near field response such as gold or silicon such that both the sample $\sigma_{n,sample}(\lambda)$ and reference $\sigma_{n,ref}(\lambda)$ spectra can be extracted from the series of single wavelength pictures. As used herein normalized spectra corresponding to or $\sigma_{n,sample}(\lambda)/\sigma_{n,ref}(\lambda)$ are referred to as $\eta_n(\lambda)$.

However, it has been found that difficulties exist in perfectly replicating the tuning of the wavelength of a light source, such as a quantum cascade laser, which renders the acquisition of spectra of both magnitude and phase of the near-field signal by sweeping difficult if not impossible.

Temporarily disregarding the characteristics of the laser itself, the spectral resolution of a spectrum recorded by a wavelength sweep is defined by the interplay between two parameters; the rate at which the laser changes wavelength, and the integration time of the measurement of the near-field signal, e.g. by the pseudo-heterodyne technique. Typically experiments can be conducted with commercial devices using sweep rates of approximately 20 $cm^{-1}/s$ and integration times of 6.5 ms (a value limited by the oscillation frequency of the reference mirror, e.g. the commercial Neaspec PMDK-2 module), corresponding to a nominal spectral resolution of around 0.13 $cm^{-1}$. Signal-to-noise considerations typically require averaging over a number of data points to allow an actual spectral resolution of around 2 $cm^{-1}$.

A single near-field phase spectrum, $\phi_3(\lambda)$, of a silicon surface recorded with a wavelength sweep covering the entire tuning range of a commercially available QCL, is shown in FIG. 3(a). A pseudo-heterodyne detection scheme is employed as known in the art and as shown in FIG. 1. It is clear that the spectrum shown in FIG. 3(a) has a large distribution of values. This spread can be understood by looking at the different contributions to the measured near-field phase, $\phi_3(\lambda)$, as shown in Eq. 1:

$$\phi_3(\lambda)=\phi_{NF}(\lambda)+\phi_{PROP}(\lambda) \quad (1)$$

$\phi_{NF}(\lambda)$ represents the contribution of the near-field interaction between the probe and the sample (which is a constant value for a spectrally flat material such as silicon and can hence be neglected in the present case) and $\phi_{PROP}(\lambda)$ represents the contribution which arises from the difference in propagation length between the two arms of the interferometer (the propagation phase). The path lengths of the two interferometer arms are labeled (4) and (5) in FIG. 1, in the following the difference if of (4) and (5) is referred to as d. For the measurements in FIGS. 3(a) and (b), d was set to 2 cm, a typical value for an unmodified commercial s-SNOM (NeaSNOM, Neaspec). With this relatively large path difference, the change in the measured phase between wavelengths is also large. This means that as the wavelength is swept, $\phi_{PROP}(\lambda)$ introduces a very fast phase ramp that obscures entirely $\phi_{NF}(\lambda)$. A wavelength change of 0.5 $cm^{-1}$, for example, leads to a phase jump of $4\pi$ in $\phi_{PROP}(\lambda)$. The propagation phase, therefore, explains the broad distribution of the measured values of $\phi_3(\lambda)$ between $-\pi$ and $\pi$ in FIG. 3(a).

In theory, the large spread of a near-field spectrum is not problematic; all s-SNOM measurements must be normalized. If the laser sweep was perfectly reproducible, each point within the spectrum would have exactly the same propagation phase $\phi_{PROP}(\lambda)$ from sweep to sweep—the propagation phases should cancel, and the remaining phase of the normalized spectrum $\eta_3(\lambda)$ should depend purely on the near-field interaction $\phi_{NF}(\lambda)$ between the probe and the sample. FIG. 3(b) shows the results of a repeatability test in practice, in essence a normalization of one spectrum on silicon to another. Although the spread of values is smaller in this "normalized" case than in that of a single sweep, the range of values is still big, and this would mask all but the biggest of changes in $\phi_{NF}(\lambda)$, which is what should be measured. Such an inability to reproduce the near-field phase spectrum $\phi_3(\lambda)$ in two identical measurements on silicon suggests a lack of repeatability in the wavelength sweep of our QCL—the lasing wavelength at any given moment obviously varies slightly from sweep to sweep, and these small fluctuations in the wavelength introduce non-reproducible variations in the propagation phase.

This may be explained by the mechanical process that is applied for tuning the wavelength. The commercial laser as used is arranged in an external cavity configuration, meaning that the wavelength is selected by use of an angled diffraction grating as part of the laser cavity. A stepper motor with a non-zero repositioning error controls the angle of this diffraction grating, and as such, no two wavelength sweeps are precisely alike. This repositioning error therefore seems the root cause of the unrepeatability of the near-field phase spectra $\phi_3(\lambda)$.

It now has surprisingly been found that by reducing the difference of the path lengths of the two interferometer arms d, the unavoidable error in the wavelength repeatability of the light source, which the root cause of the unrepeatability of the near-field phase spectra, can be overcome. In particular the unavoidable error in the wavelength repeatability of the light source can be compensated or becomes easily correctable by limiting the difference of the lengths of the two optical paths of the interferometer to values equal to or below 1 mm. The results of such a setup can be seen in the FIG. 3(c), which shows another single phase spectrum, $\phi_3(\lambda)$, on silicon where the path length was set small (crosses) and zero (dots). With a small difference, a regular ramp is observed as the phase cycles from $-\pi$ to $\pi$ several times during the sweep (which can easily be corrected), while at d=0 (known in the art as white light position, WLP), the phase is completely decoupled from the wavelength and remains at a constant value, as shown in FIG. 3(d). It is clear that slight differences in the wavelength from sweep to sweep no longer lead to a broad distribution of phases, and two separate measurements can be reliably matched as sample and reference spectra during the calculation of the normalized near-field spectrum $\eta_3(\lambda)$.

Therefore the present invention relates to a device for the near-field optical measurement of a sample comprising a probe (1), a wavelength-tunable monochromatic light source (2) with tuning mechanism for changing the wavelength $\lambda$ provided by the light source, an interferometer integrated in the optical path of the light source (2), comprising a beam splitter (3) splitting the light of the light source into two optical light paths, the reference light path (4) and the signal light path (5), wherein the reference light path (4) does not contain the probe, and the signal light path (5) comprises the probe (1), and the reference and the signal light paths (4,5) are superimposed at the detector (6), wherein the difference d of the lengths of the two optical light paths (4) and (5) can be adjusted to be at most 1000 µm. Preferably the difference d of the lengths of the two optical paths is at most 100 µm, more preferably at most 10 µm.

In one preferred embodiment in the interferometer the reference light path (4) comprises a reference mirror (7) directing the reference light path (4) via the beam splitter (3) to the detector (6), and the signal light path (5) is reflected at the probe (1) and directed via the beam splitter (3) to the detector (6). That is, in this embodiment the interferometer is of the Michelson interferometer type, integrated in the optical path of the light source (2), comprising a beam splitter (3) splitting the light of the light source into two optical paths, the reference light path (4) and the signal light path (5), wherein the reference light path (4) comprises a reference mirror (6), and the signal light path (5) comprises the probe (1). A Michelson interferometer is known in the art, and is a common configuration for optical interferometry. An exemplified embodiment of this setup is shown in FIG. 1.

In a further preferred embodiment in the interferometer the reference light path (4) is directed, preferably via a (reference) mirror (7), via a second beam splitter (8) to the detector and the signal light path (5) is reflected at the probe (1) and directed via the second beam splitter (8) to the detector (6). That is, in this embodiment the interferometer is of the Mach-Zehnder-type. Preferably, the reference light path is first reflected by a reference mirror (7) followed by the second beam splitter (8). An exemplified embodiment of this setup is shown in FIG. 2.

While it may not be a trivial task to position the interferometer of an s-SNOM system exactly in the WLP as discussed above, in accordance with the present invention a certain deviation from the WLP is acceptable as the resulting phase difference can be corrected. Typically, when setting the distances of the lengths of the interferometer arms, the path length of the interferometer arm leading to the probe and sample (the signal arm (5)) will vary each time the probe is replaced. As a result, the path leading to the mirror (the reference arm (4)) preferably is changeable e.g. with a differential micrometer screw. The WLP can be found by monitoring the phase of the s-SNOM signal on a spectrally flat sample (e.g. silicon or gold) and sequentially stepping the wavelength of the light source. Each wavelength step results in a phase jump, and this jump should be minimized by changing the length of the reference arm. Once a sufficiently small phase jump is achieved, the size of the wavelength step can be increased and the process repeated to further improve the precision of the interferometer positioning. Note that the WLP can only be determined according to this described process if the light source's wavelength can be changed, but not if only one wavelength is available.

As explained previously, the WLP is not an absolute requirement for single wavelength imaging (although it would help prevent wavelength instabilities during a scan from affecting images). It only becomes important when two measurements—each having an uncertainty in wavelength—must be compared, as in the case of sample and reference spectra for the calculation of normalized near-field spectra $\eta_3(\lambda)$. Until the introduction of wavelength-sweeping spectroscopy therefore, it has not been a requirement to operate an s-SNOM coupled to a single wavelength source in the WLP. As a result, the WLP has not been mentioned in prior art, and neither do state-of-the-art commercial s-SNOMs (e.g. NeaSNOM, Neaspec) employ the WLP in their design, nor do they currently include the facility to find it.

Suitable wavelength-tunable monochromatic light sources to be used in the device of the present invention are known in the art. The light source has to be capable of providing light, preferably laser light of a wavelength $\lambda_s$ at a time and must be capable of being tuned to provide light, preferably laser light, of a different wavelength $\lambda_t$, wherein $\lambda_s$ is different from $\lambda_t$. Preferably the light source is step-tunable between different wavelengths more preferably at least 10, even more preferably at least 100 different wavelength. Preferably the light source is a tunable quantum cascade laser or a tunable diode laser.

In one embodiment of the present invention the difference of the lengths of the two optical light paths (4) and (5) in µm is at most $2500/\Delta\lambda\pi$, wherein $\Delta\lambda$ is the wavelength accuracy (in cm$^{-1}$) of the tuning of the light source between the different wavelengths $\lambda$. That is, for a value of the wavelength accuracy $\Delta\lambda$ of 1 cm$^{-1}$ the value for d would be about 796 µm, for $\Delta\lambda$ of 0.5 cm$^{-1}$ the value for d would be about 1592 µm. The limit for the value d of $2500/\Delta\lambda\pi$ translates to a phase error of 1 radian (about 70 degrees) in the measurement of the near-field phase $\phi_3(\lambda)$ for a given wavelength accuracy $\Delta\lambda$ of the laser. The wavelength accuracy (in cm$^{-1}$) of the tuning of the light source is known for the commercially available light sources, such as the preferably used light sources such as a tunable quantum cascade laser or a tunable diode laser, or can be measured by standard means, e.g. for the laser used in the Examples of the present invention (Daylight Solutions, TLS-41066) the wavelength accuracy is given as 0.1 cm$^{-1}$.

The devices according to the present invention are devices for the near-field optical measurement of a sample. This measurement is preferably conducted by scanning (scan-probing) the sample with the probe while measuring the near-field interaction between the probe and the sample by detecting the scattering of light focused on to the tip of the scanning probe during scanning.

Probes to be used in the devices according to the present invention are probes comprising a cantilever and a tip, which are known in the art for AFM or for scanning near-field optical microscopy (SNOM). These probes typically comprise a cantilever which carries the tip on one of its ends, the other end of the cantilever is typically mounted onto a larger base to simplify mounting and replacement of the tip. The radius of curvature of the tip is typically below about 100 nm, preferably below about 50 nm, most preferably below about 20 nm. The tips of the cantilevers may be metalized. These probes comprising suitable tips are commercially available, e.g. from NANOSENSORS™ or MikroMasch.

The device according to the present invention typically comprises a sample table or holder as known in the art. This table or holder is preferably able to fix the sample and to move the sample in (sub-)nanometer range, e.g. by piezoelectric devices. Alternatively, the sample is fixed in the device and the holder of the cantilever is able to move the cantilever carrying tip in (sub-)nanometer range.

Suitable beam splitters, as well as mirrors are commercially available. The difference d of the lengths of the two optical light paths (4) and (5) (cf. FIGS. 1 and 2) in the interferometer as installed in the device of the present invention is at most 1000 µm. As only the difference of the paths is relevant, these parts of the paths where the two paths (4) and (5) are superimposed are not considered herein. That is, the difference of the lengths of the two optical light paths (4) and (5) in the Michelson interferometer type as used herein is as indicated in FIG. 1 the difference in the lengths of the optical paths, measured from the beam splitter to the reference mirror in the reference light path (4) and from the beam splitter to the probe in the signal light path (5), respectively. The difference of the lengths of the two optical light paths (4) and (5) in the Mach-Zehnder interferometer type as indicated in FIG. 2 is the difference in the lengths of the optical paths, measured from the beam splitter, optionally via the reference mirror (7) to the second beam splitter in the reference light path (4) and from the beam splitter to the probe and to the second beam splitter in the signal light path (5), respectively. Within the paths additional mirrors, except for the reference mirror in the reference path, might be present, which are to be ignored as these do not change the actual length of the path(s) but only change the direction of the path. For the "length" of the path as used herein the actual way the light propagates is considered relevant.

In one preferred embodiment the device uses suitable methods for reducing the background signal (background suppression), preferably pseudo-heterodyne detection as known in the art in particular in the Michelson interferometer type. That is, preferably the probe is capable of being mechanically oscillated at a frequency $\Omega$ and a mirror, preferably the reference mirror is capable of being mechanically oscillated in the direction of the light path, preferably the reference light path (4) at a frequency M. Preferably, frequency M is lower than $1/10$ of the frequency $\Omega$. Preferred embodiments of pseudo-heterodyne detection are disclosed in WO 2007/039210 A, which is incorporated by reference herein.

In one preferred embodiment of the present application, the device further comprises a primary mirror. The primary mirror to be used in the device according to the present invention is a concave mirror. The shape of the concave, reflective area of the mirror is such that the light of independent optical pathways can be focused onto the probe. Therefore the primary mirror is preferably arranged such that the concave side of the mirror faces the probe and the probe is preferably positioned in the focal point of the concave primary mirror.

In a preferred embodiment the primary mirror of the device of the present invention is a parabolic mirror, in particular a parabolic mirror as disclosed in DE 10 2006 002 461 A1.

In one embodiment, the device according to the present invention further comprises an optical monitoring system, which is arranged to monitor the sample and/or the alignment of deflection detection system of the cantilever. Such monitoring systems are known in commercially available AFM microscopes and typically comprise an optical detection system or an optical access to be used by eye to the top of the cantilever. The systems are typically used in order to ensure that the laser, which is usually applied for the detection of the deflection of the cantilever, is correctly aligned and focused onto the backside of the cantilever.

The invention further relates to a method for scanning (scan-probing) the optical near field of a sample, wherein preferably the device as described above is used. The present invention thus relates to a method for measuring at least one component of the near-field interaction of a probe with the sample using a device according to any of the above described embodiments comprising a probe (1), a wavelength-tunable monochromatic light source (2) with tuning mechanism for changing the wavelength λ provided by the light source, an interferometer integrated in the optical path of the light source (2), comprising a beam splitter (3) splitting the light of the light source into two optical paths, the reference light path (4) and the signal light path (5), wherein the reference light path (4) does not comprise the probe (1) and the signal light path (5) comprises the probe (1), and the reference and the signal light paths (4, 5) are superimposed at the detector (6) wherein the difference of the lengths of the two optical light paths (4) and (5) is at most 1000 μm, the method comprising the step of bringing the probe into the proximity of the sample at at least one position, wherein in each position the light source is tuned to provide laser light of at least two different wavelengths and at each wavelength at least one component of the near-field interaction of the probe with the sample is measured before changing the position of the probe on the sample.

That is, in the methods according to the present invention, at each investigated pixel (position) at least one component of the near-field interaction of a probe with the sample is measured, preferably both magnitude and phase, at preferably at least two, preferably at least 5, in particular at least 10 wavelengths. After determining this data, the probe is moved to the next pixel (position) to be investigated, followed by measuring at least one component of the near-field interaction of the probe with the sample. Typically sample height, i.e the topography of the sample, is measured at the same time, but may also be measured before to determine special points of interest of the sample, which are then approached by the probe to measure the components of the near-field interaction, preferably at several wavelength.

The present invention further relates to a method for measuring at least one component of the near-field interaction of a probe with the sample using a device according to any of the above described embodiments comprising a probe (1), a wavelength-tunable monochromatic light source (2) with tuning mechanism for changing the wavelength λ provided by the light source, which is a tunable quantum cascade laser or a tunable diode laser an interferometer integrated in the optical path of the light source (2), comprising a beam splitter (3) splitting the light of the light source into two optical paths, the reference light path (4) and the signal light path (5), wherein the reference light path (4) does not comprises the probe (1), and the signal light path (5) comprises the probe (1), and the reference and the signal light paths (4, 5) are superimposed at the detector (6) the method comprising the step of bringing the probe into the proximity of the sample at at least one position, wherein in each position the light source is tuned to provide laser light of at least two different wavelengths and at each wavelength at least one component of the near-field interaction of the probe with the sample is measured before changing the position of the probe on the sample.

Preferred light sources, device parts, as well as difference of the lengths of the two optical light paths (4) and (5) as used in the methods of the invention are those as describe above for the device of the invention.

Preferably, in the methods of the invention both the phase and the amplitude are measured as components of the near-field interaction of the probe with the sample before changing the position of the probe on the sample.

The invention relates further to the use of a device as described above for scanning the optical near-field of a sample.

The device of the present invention is provided with at least one light source device to provide focused light, which light is scattered at tip of the probe in order to conduct the near-field measurement. Preferably this illumination of the tip of the probe is via the primary mirror. The mirror optic, i.e. all the mirrors used comprising the primary mirror and the reference mirror, and the light source device are preferably fixable in relation to each other so that where the system once has been adjusted, no further adjustments during an optical near-field measurement are necessary.

The device according to the present invention is also provided with a detector by which the light scattered by the near-field probe can be detected. Suitable detectors are known in the art. The mirror optic used according to the invention advantageously detects a large spatial angle to collect the light scattered at the near-field probe, which leads to high collection efficiency and an improved signal-to-noise ratio. The spatial angle covered by the primary mirror corresponds to a large cross-section of optionally parallel beams on the independent optical pathways. As the parallel beams on each independent optical pathway are typically not compact but deformed in the form of a rectangle or elongated, a division of the parallel beam into two or more beams on each independent optical pathway extending adjacently may be provided. Several beams may thus be advantageously directed on to the near-field probe in this way or the light scattered back may thus be detected with spatial resolution.

The figures and the following example illustrate further details and advantages of the invention.

Figure 3:
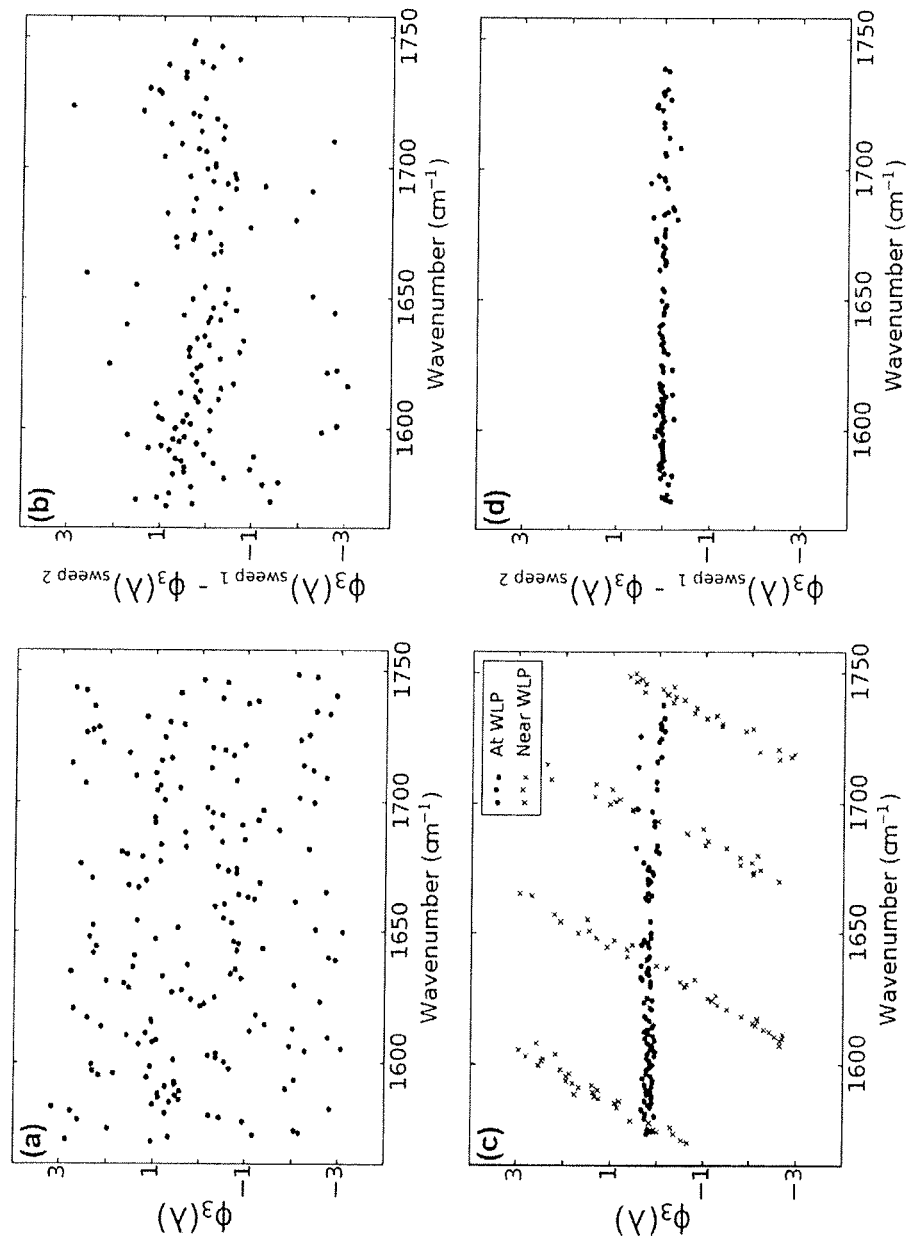

FIG. 3 shows near field phase spectra. (a) shows a near-field phase spectrum $\phi_3(\lambda)$ of a single QCL wavelength sweep on a silicon surface where the path length difference is large (>2 cm). (b) shows a repeatability test of two sweeps with a large path length difference (>2 cm). (c) shows the same measurement as (a), but with the path length difference small (crosses) and zero (dots). (d) shows a repeatability test performed with the path length difference zero.

Figure 4:
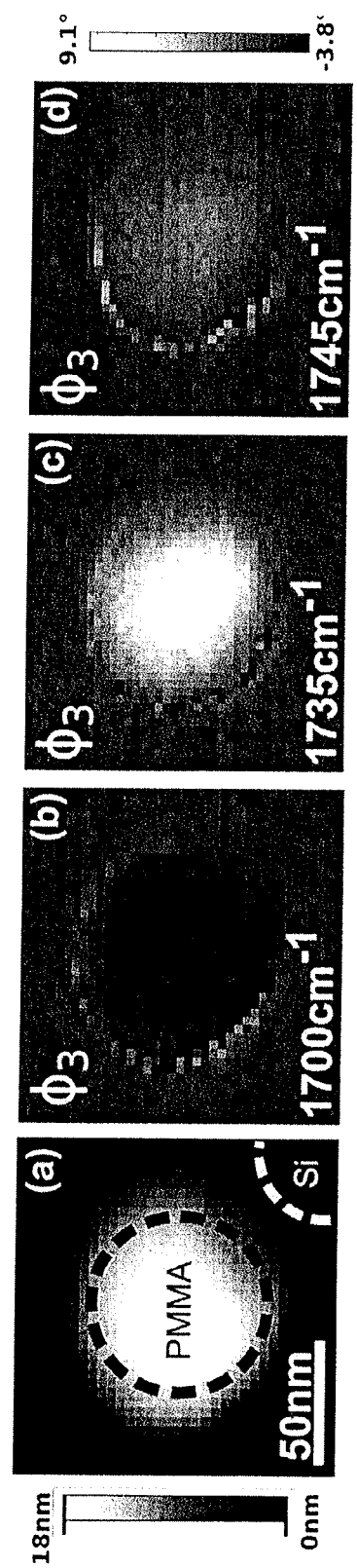

FIG. 4(a) shows the topography of an 18 nm thick PMMA disc. (b-d) show a selection of the near-field phase $\phi_3$ images of the same disc taken at 1700, 1735 and 1745 cm-1 respectively, where the phase on silicon has been set to zero.

Figure 5:
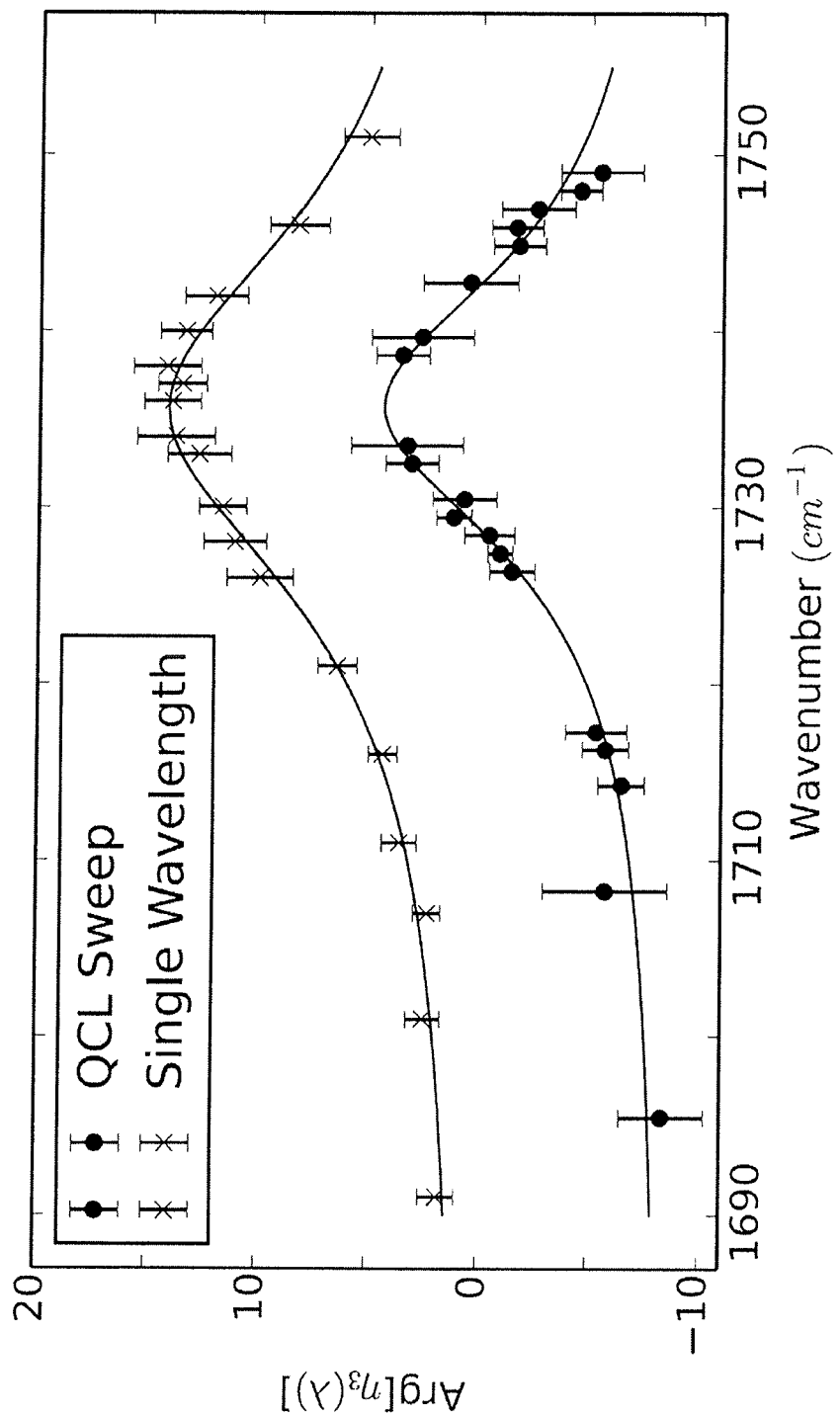
Figure 6:
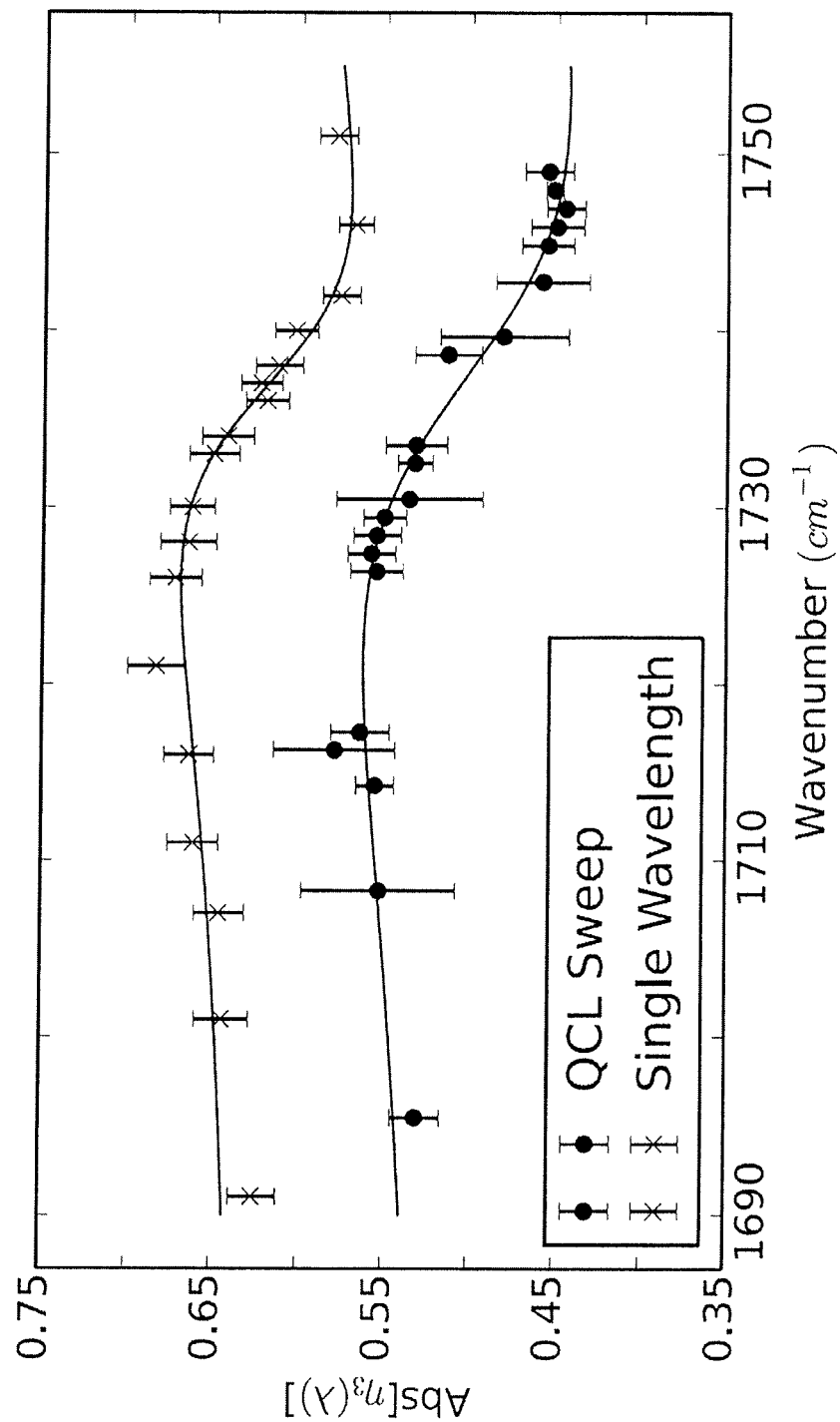
Figure 7:
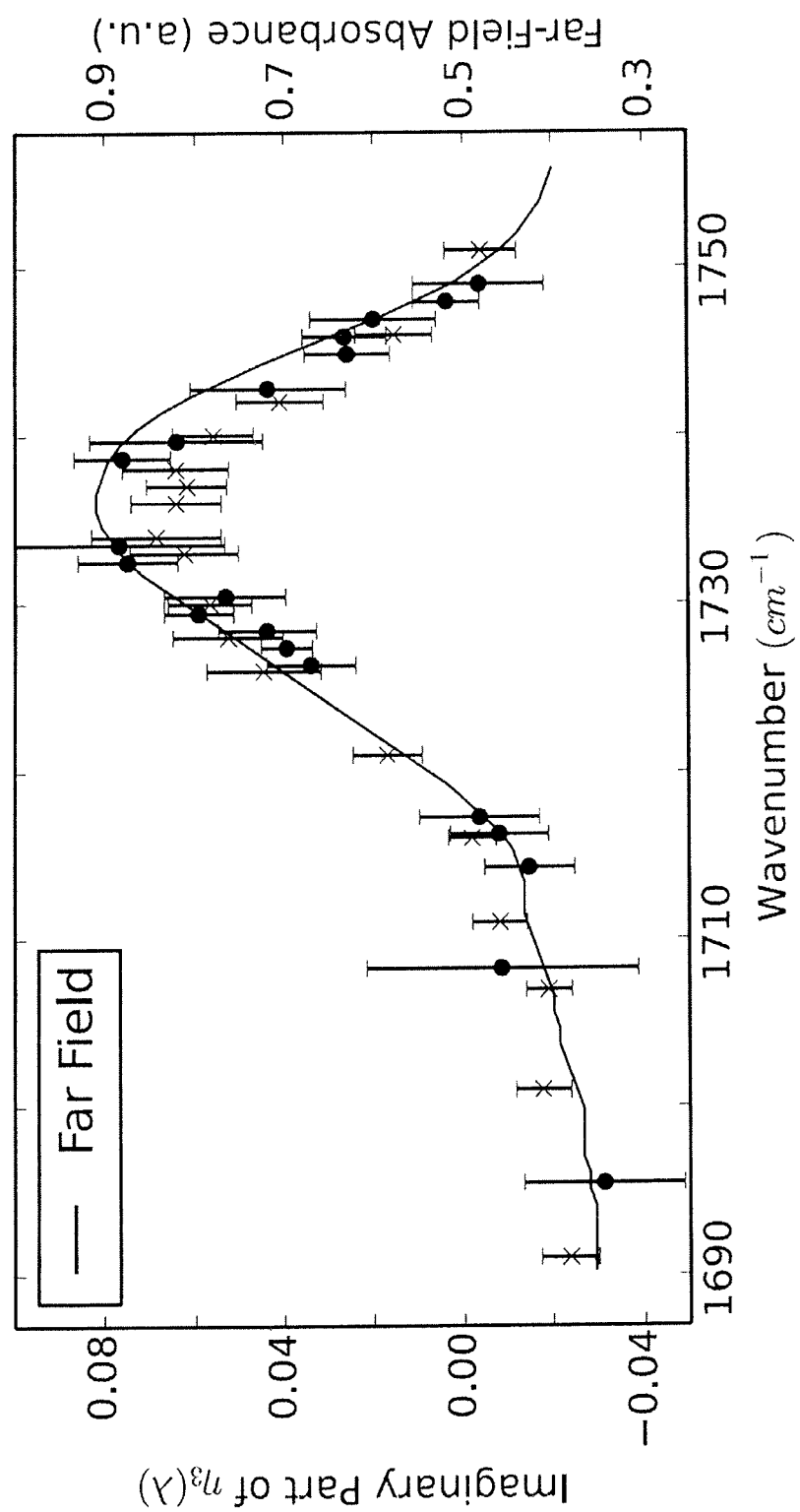

FIGS. 5 to 7 show the normalized phase, magnitude and imaginary part spectra extracted from a series of single wavelength images (crosses) and the wavelength sweeping technique according to the present invention (dots). For clarity, the single wavelength and wavelength swept curves have been offset by ±5 degrees and ±0.05 in the phase and magnitude spectra respectively. The solid lines are Lorentzian curve fits—these are not intended to be precise representations of the underlying data but rather guides to the eye.

EXAMPLE

Figure 1:
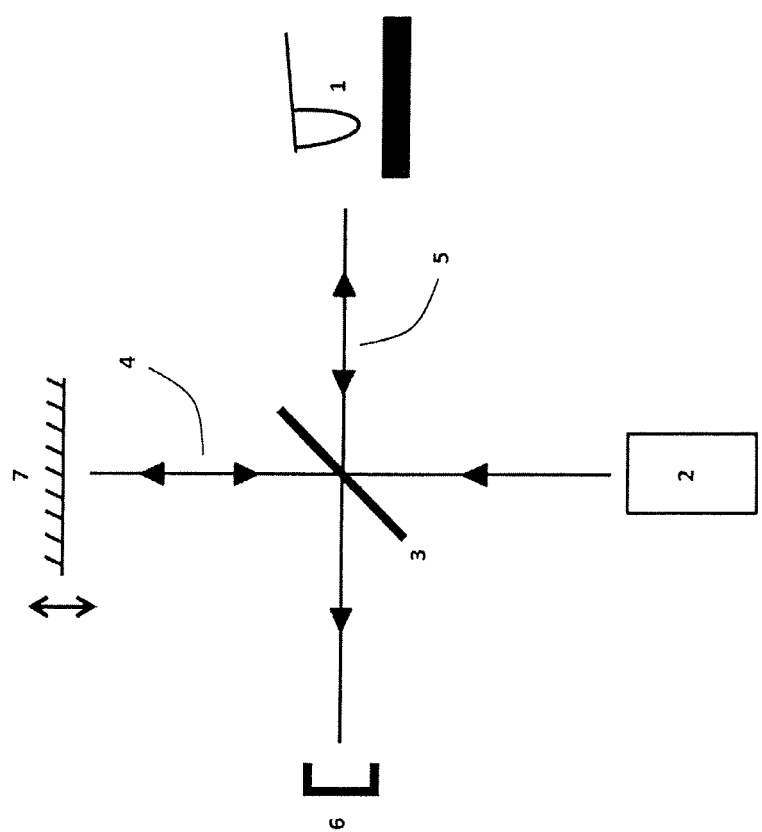
FIG. 1 is a schematic of the pseudo-heterodyne near-field detection system as employed for the wavelength swept spectroscopy of the present invention using a Michelson interferometer type.
Figure 2:
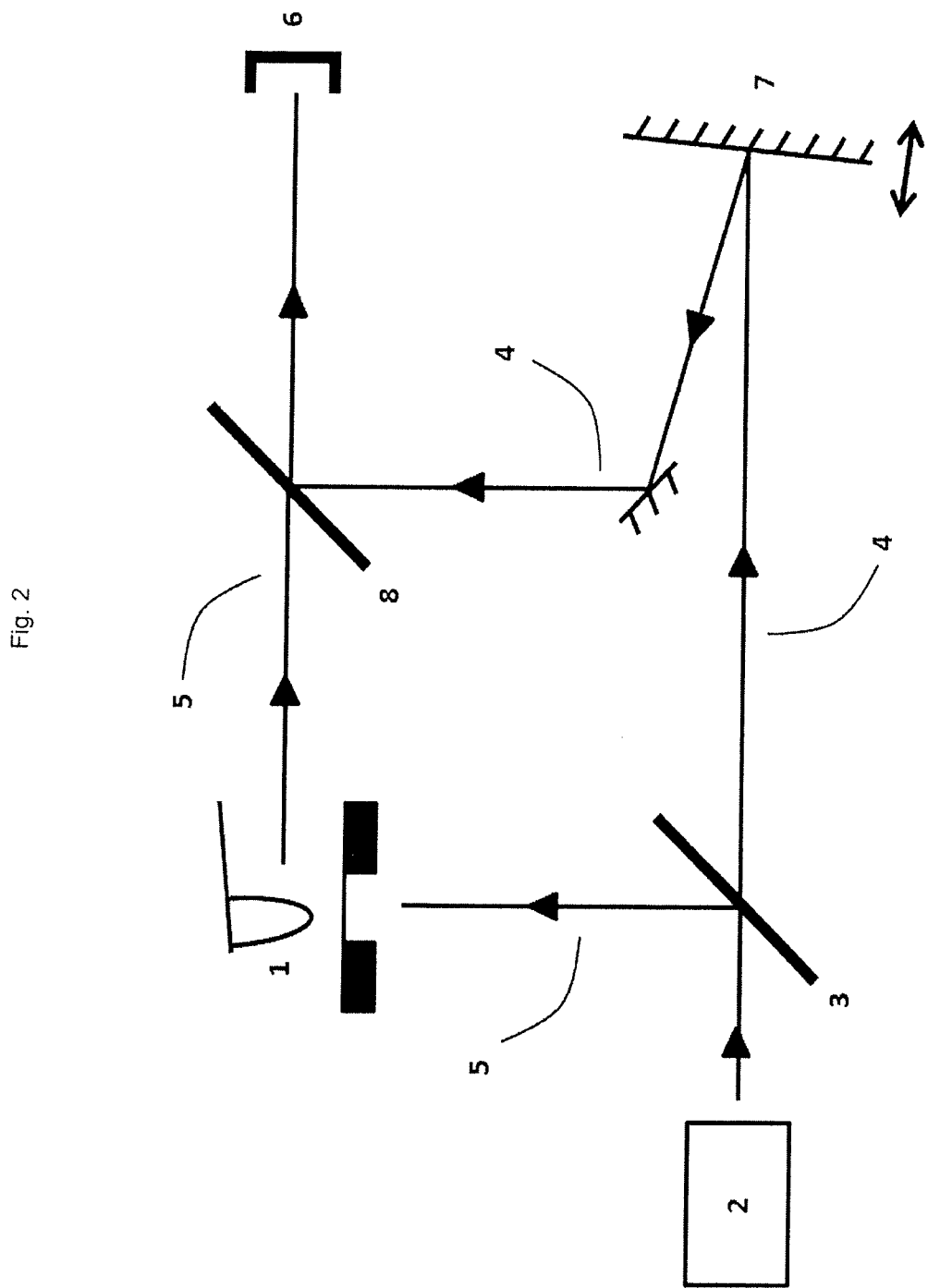
FIG. 2 is a schematic of a near-field detection system using a Mach-Zehnder interferometer type.

Experimental S-SNOM Setup:

The experimental setup is based on the widely used pseudo-heterodyne detection scheme as implemented on a commercially available s-SNOM (NeaSNOM, Neaspec), a schematic for which is shown in FIG. 1. In more detail, continuous wave (CW) light emitted by the QCL (CW-PLS Laser, Daylight Solutions) as light source (2) passes through a beamsplitter (3) where it forms two beams. The first beam—the signal arm (5)—continues to an off-axis parabolic mirror where it is focused to the apex of an oscillating metallic probe (1) (oscillation frequency $\Omega$ typically in the hundreds of kilohertz) which acts as an optical antenna by both confining, and subsequently scattering, the field in its immediate vicinity. The same parabolic mirror collects and re-collimates the backscattered light. The second beam—the reference arm (4)—is phase modulated by reflection from a vibrating mirror (7) (oscillation frequency M typically a few hundred hertz). Both arms (4, 5) are recombined and focused on to a nitrogen-cooled mercury-cadmium-telluride (MCT) detector (6) (FTIR-16-0.1, Infrared Associates)

Results on PMMA Discs:

As a proof-of-principle experiment that the wavelength sweeping technique of the present invention is capable of collecting high-resolution infrared absorption spectra, experimental results from a simple sample—a polymer disc (poly-(methyl methacrylate), or PMMA) on a silicon substrate prepared by colloidal lithography are provided—and compared to a "traditional" near-field spectrum gathered from a series of single wavelength images. PMMA is known to absorb strongly near 1730 cm$^{-1}$ due to C=O double bond stretching, and so it is expected to measure a peak in the imaginary part of $\eta_3(\lambda)$ at these wavelengths. The studied disc was slightly under 20 nm in height, and 100 nm in diameter, as can be seen in the topography shown in FIG. 4(a).

FIG. 4(b), (c) and (d) show the near-field phase $\phi_3$ of single wavelength measurements at 1700, 1735 and 1745 cm$^{-1}$. These phase data indicate the local absorption. As expected, the images clearly show stronger contrast close to the C=O absorption peak with a maximum phase contrast of 9° (as compared to the silicon substrate) at 1735 cm$^{-1}$. The above curves (crosses) in FIGS. 5, 6 and 7 show the magnitude, phase and imaginary parts respectively of the normalized near-field signal $\eta_3(\lambda)$. Their values are extracted by averaging over the pixels containing the PMMA and the substrate in each image as outlined in the topography image FIG. 4(a) by a dashed circle. The error bars show the standard deviation of the pixel values used in the averaging.

The lower curves (dots) in FIGS. 5 and 6 are found using the wavelength sweeping method. For these measurements the laser was swept from 1690 to 1750 cm$^{-1}$ a total of 30 times while the probe was on the PMMA, and 20 times on the silicon. Every sweep took 2.8 seconds meaning a total measurement time of slightly less than 2.5 minutes. To extract the near-field spectrum $\sigma_3(\lambda)$, the sweeps were first divided up into time bins of 70 ms (corresponding to a spectral resolution of 1.5 cm$^{-1}$ as a number of wavelength steps occur within the bin). The value of each time bin—also corresponding to a wavelength—was calculated by finding the median average of the pseudo-heterodyne measurements within it. The mean and standard deviation of each bin was then found by combining the individual sweeps (i.e. 30 on PMMA, 20 on silicon), leaving a single spectrum for each material with a measure of the error at each wavelength $\sigma_3(\lambda)\pm err(\lambda)$. Next, the PMMA spectrum was normalized to the silicon spectrum and the magnitude, phase and imaginary parts of $\eta_3(\lambda)$ extracted. Finally, data points where the phase error bars exceeded 8° were excluded for visual clarity, resulting in blank areas in the spectrum.

In FIG. 7—where the imaginary parts of the individual images and the wavelength sweeping method are overlaid—close agreement is seen, proving that the wavelength sweeping technique is effective for rapidly gathering near-field spectra. The slightly lower peak in the single wavelength spectrum is likely due to averaging over an area of non-uniform PMMA height leading to a variation in the strength of the local absorption. In both cases, the peak maximum at 1735 cm$^{-1}$ shows excellent agreement with the far-field absorption spectrum, which was taken using grazing incidence Fourier transform infrared spectroscopy (GI-FTIR). It is also evident that some wavelengths that are accessible in single wavelength imaging exhibit large measurement errors in the wavelength sweeping spectra; this may be due to an insufficient laser settling time during the sweep causing either a low or a highly variable power output.

It is also noted that while a constant reference mirror vibration amplitude during the wavelength sweep might introduce a systematic error to the measurement, this can be minimized by adjusting the vibration amplitude for the central wavelength of the sweep; the error is largest at the spectral extremes. For the tuning range of the laser used, however, its effect is negligibly small, as can be seen from the excellent agreement of the wavelength-swept spectra with both the single wavelength spectra (where the reference mirror vibration amplitude was adjusted for each wavelength) and with the GI-FTIR data.

It is to be noted that from the y scale of FIG. 7 it may seem counter-intuitive that the imaginary part of the normalized near-field spectrum $\eta_3(\lambda)$ can have negative values. The source of this is the relative phases of the sample and reference spectra—if the measured near-field phase, $\phi_3$, of the silicon is larger than that of the PMMA, then the normalization procedure yields a negative value for the phase which, in turn, leads to a negative imaginary part of $\eta_3(\lambda)$. For wavelengths away from the absorption peak of PMMA, this can be seen to be the case, both in the phase spectrum of FIG. 7 and in the single wavelength image at 1700 cm$^{-1}$ of FIG. 4(b). This means that the probe-surface interaction for silicon introduces a slightly larger phase delay in the scattered light than that for PMMA (for off-resonant wavelengths). Speculatively, it may be assumed that the reason for this delay could be either a shift in the antenna resonance of the probe as it is loaded upon approaching the surface, or because the tip is also illuminated by reflection from the sample (as well as direct illumination) and hence can be affected by sample topography. For the purposes of the normalization, however, it is only required that the near-field phase response of the silicon be spectrally flat. Its absolute value (i.e. whether it is greater or less than the near-field phase response of PMMA) is inconsequential, and only matters insofar as dictating the sign of the normalized spectrum.

The invention claimed is:

1. Device for the near-field optical measurement of a sample comprising
   a. a probe (1),
   b. a wavelength-tunable monochromatic light source (2) with tuning mechanism for changing the wavelength $\lambda$ provided by the light source, and
   c. an interferometer integrated in the optical path of the light source (2), comprising a beam splitter (3) splitting the light of the light source into two optical light paths, the reference light path (4) and the signal light path (5), wherein the reference light path (4) does not contain the probe, and the signal light path (5) comprises the probe (1), and the reference and the signal light paths (4,5) are superimposed at the detector (6), characterized in that the difference of the lengths of the two optical paths (4) and (5) can be adjusted to be at most 1000 µm.

2. Device according to claim 1, wherein in the interferometer the reference light path (4) comprises a reference mirror (7) directing the reference light path (4) via the beam splitter (3) to the detector (6), and the signal light path (5) is reflected at the probe (1) and directed via the beam splitter (3) to the detector (6), or wherein in the interferometer the reference light path (4) is directed by a second beam splitter (8) to the detector and the signal light path (5) is reflected at the probe (1) and directed via the second beam splitter (8) to the detector (6).

3. Device according to claim 1, wherein the difference of the lengths of the two optical paths (4) and (5) can be adjusted to be at most 100 µm.

4. Device according to claim 1, wherein the difference of the lengths of the two optical paths (4) and (5) can be adjusted to be at most 10 µm.

5. Device according to claim 1, wherein the difference of the lengths of the two optical paths (4) and (5) in µm can be adjusted to be at most $2500/\Delta\lambda\pi$, wherein $\Delta\lambda$ is the wavelength accuracy (in cm$^{-1}$) of the tuning of the light source between the different wavelengths $\lambda$.

6. Device according to claim 1, wherein the light source is a tunable quantum cascade laser or a tunable diode laser.

7. Method for measuring at least one component of the near-field interaction of a probe with the sample using a device according to claim 1 comprising a probe (1),
   a wavelength-tunable monochromatic light source (2) with tuning mechanism for changing the wavelength $\lambda$ provided by the light source, and
   an interferometer integrated in the optical path of the light source (2), comprising a beam splitter (3) splitting the light of the light source into two optical light paths, the reference light path (4) and the signal light path (5), wherein the reference light path (4) does not contain the probe, and
   the signal light path (5) comprises the probe (1), and the reference and the signal light paths (4,5) are superimposed at the detector (6), wherein the difference of the lengths of the two optical paths (4) and (5) is at most 1000 µm,
   the method comprising the step of bringing the probe into the proximity of the sample at at least one position, wherein in each position the light source is tuned to provide laser light of at least two different wavelengths and at each wavelength at least one component of the near-field interaction of the probe with the sample is measured before changing the position of the probe on the sample.

8. Method according to claim 7, wherein in the interferometer the reference light path (4) comprises a reference mirror (7) directing the reference light path (4) via the beam splitter (3) to the detector (6), and the signal light path (5) is reflected at the probe (1) and directed via the beam splitter (3) to the detector (6), or
   wherein in the interferometer the reference light path (4) is directed by a second beam splitter (8) to the detector and the signal light path (5) is reflected at the probe (1) and directed via the second beam splitter (8) to the detector (6).

9. Method according to claim 7, wherein the light source is a tunable quantum cascade laser or a tunable diode laser.

10. Method according to claim 7, wherein the difference of the lengths of the two optical paths (4) and (5) is at most 100 µm.

11. Method according to claim 7, wherein the difference of the lengths of the two optical paths (4) and (5) is at most 10 µm.

12. Method according to claim 7, wherein the difference of the lengths of the two optical paths (4) and (5) in µm is at most $2500/\Delta\lambda\pi$, wherein $\Delta\lambda$ is the wavelength accuracy (in cm$^{-1}$) of the tuning of the light source between the wavelengths.

13. Method according to claim 7, wherein both phase and amplitude are measured as components of the near-field interaction of the probe with the sample before changing the position of the probe on the sample.

14. Method for measuring at least one component of the near-field interaction of a probe with the sample using a device according to claim 1 comprising a probe (1),
- a wavelength-tunable monochromatic light source (2) with tuning mechanism for changing the wavelength λ provided by the light source, which is a tunable quantum cascade laser or a tunable diode laser, and
- an interferometer integrated in the optical path of the light source (2), comprising a beam splitter (3) splitting the light of the light source into two optical light paths, the reference light path (4) and the signal light path (5),
- wherein the reference light path (4) does not contain the probe, and
- the signal light path (5) comprises the probe (1), and the reference and the signal light paths (4,5) are superimposed at the detector (6),
- the method comprising the step of bringing the probe into the proximity of the sample at at least one position, wherein in each position the light source is tuned to provide laser light of at least two different wavelengths and at each wavelength at least one component of the near-field interaction of the probe with the sample is measured before changing the position of the probe on the sample.

15. Method according to claim 14, wherein in the interferometer the reference light path (4) comprises a reference mirror (7) directing the reference light path (4) via the beam splitter (3) to the detector (6), and the signal light path (5) is reflected at the probe (1) and directed via the beam splitter (3) to the detector (6), or
- wherein in the interferometer the reference light path (4) is directed by a second beam splitter (8) to the detector and the signal light path (5) is reflected at the probe (1) and directed via the second beam splitter (7) to the detector (6).

* * * * *